United States Patent
Hwang et al.

(10) Patent No.: US 10,336,828 B2
(45) Date of Patent: Jul. 2, 2019

(54) FUSION POLYNUCLEOTIDE CONTAINING MURINE CMV PROMOTER AND METHOD OF PREPARING A POLYPEPTIDE OF INTEREST USING THE SAME

(71) Applicant: Samsung Bioepis Co., Ltd., Incheon (KR)

(72) Inventors: Su Jeong Hwang, Suwon-si (KR); Min-Kyung Kim, Seoul (KR); Sangjoon Park, Yongin-si (KR); Chanmoo Lee, Gwacheon-si (KR); Mi Young Cho, Seoul (KR)

(73) Assignee: SAMSUNG BIOEPIS CO., LTD., Incheon (KR)

( * ) Notice: Subject to any disclaimer, the term of this patent is extended or adjusted under 35 U.S.C. 154(b) by 267 days.

(21) Appl. No.: 14/961,441

(22) Filed: Dec. 7, 2015

(65) Prior Publication Data

US 2016/0159926 A1    Jun. 9, 2016

(30) Foreign Application Priority Data

Dec. 5, 2014    (KR) ........................ 10-2014-0174443

(51) Int. Cl.
*C12N 15/85* (2006.01)
*C07K 16/28* (2006.01)
*C07K 16/00* (2006.01)

(52) U.S. Cl.
CPC .......... *C07K 16/2863* (2013.01); *C07K 16/00* (2013.01); *C12N 15/85* (2013.01); *C12N 2830/42* (2013.01)

(58) Field of Classification Search
None
See application file for complete search history.

(56) References Cited

U.S. PATENT DOCUMENTS

| | | | |
|---|---|---|---|
| 7,794,976 B2 | 9/2010 | Handa et al. | |
| 8,545,839 B2 * | 10/2013 | Goetsch | C07K 16/2863 424/130.1 |
| 2004/0156832 A1 * | 8/2004 | Jolly | C07K 16/34 424/93.21 |
| 2007/0258962 A1 | 11/2007 | Chatellard et al. | |
| 2009/0181424 A1 | 7/2009 | Abericio et al. | |
| 2013/0089542 A1 | 4/2013 | Lee et al. | |

FOREIGN PATENT DOCUMENTS

| | | |
|---|---|---|
| CN | 1952160 A | 4/2007 |
| JP | 5209693 B2 | 6/2013 |
| KR | 2002-0040452 A | 3/2004 |
| KR | 2002-0075617 A | 5/2004 |
| KR | 2011-0047698 A | 5/2011 |
| KR | 2008-0003384 A | 9/2013 |

OTHER PUBLICATIONS

MCMV promoter, Genbank accession L06816.1 downloaded from: http://www.ncbi.nlm.nih.gov/nucleotide/330543?report=genbank &log$=nuclalign&blast_rank=1&RID=RUY42S81014 Jul. 6, 2016.*
Kim et al., Journal of Biotechnology, 2002, vol. 93, pp. 183-187.*
Xu et al., Gene, 2001, vol. 272, pp. 149-156.*
Melcher et al., BBA, 2002, vol. 1575, pp. 49-53.*
Lacy-Hulbert et al., Gene Therapy, 2001, vol. 8 pp. 649-653.*
Hermening et al., Increased protein expression from adenoviral shuttle plasmids and vectors by insertion of a small chimeric intron sequence, *Journal of Virological Methods*,122(1): 73-77 (2004).
Kim et al., The human elongation factor 1 alpha (EF-1α) first intron highly enhances expression of foreign genes from the murine cytomegalovirus promoter, *Journal of Biotechnology*, 93(2):183-187 (2002).
Huang, et al., "Intervening sequences increase efficiency of RNA 3' processing and accumulation of cytoplasmic RNA," *Nucleic Acids Research*, vol. 18, No. 4 (1990).

* cited by examiner

*Primary Examiner* — Mindy G Brown
(74) *Attorney, Agent, or Firm* — Leydig, Voit & Mayer, Ltd.

(57) ABSTRACT

A fusion polynucleotide including a murine CMV promoter and an intron, a recombinant vector including the fusion polynucleotide and a gene encoding a polypeptide of interest, a recombinant cell including the recombinant vector, and a method of producing a polypeptide of interest using the recombinant vector and/or the recombinant cell.

20 Claims, 5 Drawing Sheets

Specification includes a Sequence Listing.

①: mouse CMV promoter
②: Intorn sequence (IGLV intron, IGK Intron, IGH Intron, chimeric intron)
③: Gene of interst
④: Polyadenylation signal

FUSION POLYNUCLEOTIDE CONTAINING MURINE CMV PROMOTER AND METHOD OF PREPARING A POLYPEPTIDE OF INTEREST USING THE SAME

CROSS-REFERENCE TO RELATED APPLICATIONS

This application claims the benefit of Korean Patent Application No. 10-2014-0174443 filed on Dec. 5, 2014 in the Korean Intellectual Property Office, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted herewith and identified as follows: One 15,106 byte ASCII (Text) file named "722574_ST25.TXT" created Dec. 7, 2015.

BACKGROUND OF THE INVENTION

1. Field

Provided is a fusion polynucleotide including a murine CMV promoter and an intron, a recombinant vector including the fusion polynucleotide and a gene encoding a polypeptide of interest, a recombinant cell including the recombinant vector, and a method of producing a polypeptide of interest using the recombinant vector and/or the recombinant cell.

2. Description of the Related Art

Therapeutic proteins, such as antibodies, have emerged in the medical industry and have been developed as medicines for various targets. To commercialize therapeutic proteins and examine effects thereof, it is necessary to produce the proteins on a large scale.

The use of an animal cell to produce a therapeutic protein can increase the efficacy of the therapeutics compared to using microorganisms to produce a protein; however, animal cells are limited in that the amount of produced protein is small. To solve this problem, it is necessary to develop a recombinant vector capable of increasing the productivity of protein in an animal cell (e.g., U.S. Pat. No. 5,168,062 A).

BRIEF SUMMARY OF THE INVENTION

Provided is a fusion polynucleotide or fusion promoter including a murine cytomegalovirus (CMV) promoter and an intron. The fusion polynucleotide may be useful as a promoter, for example, a promoter operable in an animal cell (e.g., a mammalian cell).

Also provided is a recombinant vector including the fusion polynucleotide or fusion promoter including a murine CMV promoter and an intron. The recombinant vector may be useful as an expression vector capable of expressing a polypeptide of interest in a host cell, when a gene encoding the polypeptide of interest is operatively linked therein. The recombinant vector may be one capable of being expressed in a host cell. In one embodiment, the fusion polynucleotide is operatively linked to the gene encoding a polypeptide of interest.

Further provided is a recombinant cell including the recombinant vector, as well as a method for producing a polypeptide of interest using the recombinant vector or the recombinant cell.

Related methods and compositions also are provided.

DETAILED DESCRIPTION OF THE INVENTION

Figure 1:
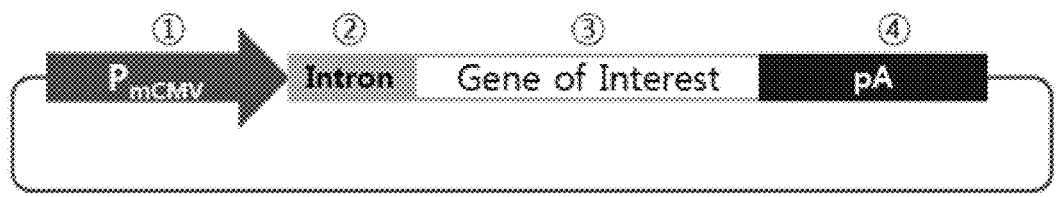
FIG. 1 is a diagram of an expression vector comprising a fusion polypeptide comprising a murine CMV promoter and intron.

This disclosure relates to a use of a murine CMV promoter and an intron in preparing a recombinant vector for producing a polypeptide of interest.

An embodiment provides a fusion polynucleotide comprising a murine CMV promoter and an intron. The fusion polynucleotide may be useful as a promoter, for example, capable of operating in an animal cell (e.g., a mammalian cell). Therefore, the fusion polypeptide may be a fusion promoter.

The murine CMV promoter may be all or a part of a murine CMV immediate-early enhancer/promoter (a murine CMV IE enhancer/promoter). The murine CMV immediate-early enhancer/promoter may comprise or consist essentially of the nucleotide sequence of SEQ ID NO: 9.

For example, the murine CMV promoter may comprise
i) a polynucleotide comprising or consisting essentially of a murine CMV IE enhancer/promoter (SEQ ID NO: 9),
ii) a polynucleotide fragment of a murine CMV IE enhancer/promoter comprising or consisting essentially of consecutive nucleotide residues of about 100 bp or more, about 200 bp or more, about 300 bp or more, about 500 bp or more, or about 700 bp or more, for example, about 100 to about 1391 bp, about 200 to about 1391 bp, about 300 to about 1391 bp, about 500 to about 1391 bp, about 700 to about 1391 bp, about 100 to about 1000 bp, about 200 to about 1000 bp, about 300 to about 1000 bp, about 500 to about 1000 bp, about 700 to about 1000 bp, about 100 to about 700 bp, about 200 to about 700 bp, about 300 to about 700 bp, or about 500 to about 700 bp, within a murine CMV IE enhancer/promoter, or
iii) a variant of human CMV IE enhancer/promoter (maintaining the function as a promoter) having a sequence identity of at least about 80%, at least about 85%, at least about 90%, at least about 95%, at least about 98%, or at least about 99% to the sequence of the polynucleotide fragment i) or ii), or further comprising nucleotide residues of about 1 to about 100 bp or about 5 to about 60 bp (each of which is independently selected from A, T, G, and C) at 5'- and, 3'-end, or both ends of the polynucleotide fragment i) or ii).

The term "intron" may refer to a non-translated and intervening nucleotide sequence located between exons which are translated into a protein after transcription. A final mature RNA product is generated by removing the non-translated region, intron, from a transcribed mRNA precursor by RNA splicing. As used herein, the term "intron" encompasses a splicing donor and recipient, a triploid guanine motif, and/or a replication fork.

The intron may be any intron isolated from a gene of an animal, for example, a mammal (e.g., human). The intron may be at least one selected from the group consisting of immunoglobulin introns (e.g., at least one selected from the group consisting of IGLV intron, IGKV intron, IGH intron, and the like), a chimeric intron, an intron A of human cytomegalovirus major immediate-early release protein gene, and the like. For example, the intron may be at least one selected from the group consisting of IGLV intron, IGKV intron, and IGH intron.

IGLV (immunoglobulin lambda variable) intron refers to an intron region of a gene encoding a variable region of lambda light chain of an immunoglobulin. For example, the IGLV intron may be a human IGLV intron (IGLV-1L1; e.g., an intron from position 71 to position 185 of Accession No. X59707; 115 bp; SEQ ID NO: 5); an intron fragment comprising or consisting essentially of consecutive nucleotide residues of about 10 to about 115 bp, about 30 to about 115 bp, about 50 to about 115 bp, about 80 to about 115 bp, about 100 to about 115 bp, about 10 to about 114 bp, about 30 to about 114 bp, about 50 to about 114 bp, about 80 to about 114 bp, or about 100 to about 114 bp within SEQ ID NO: 5; an intron variant of the intron of SEQ ID NO: 5 or an intron fragment thereof, having a sequence identity of at least about 80%, at least about 85%, at least about 90%, at least about 95%, at least about 98%, or at least about 99%, with the sequence of the intron or intron fragment; or an intron variant of the intron of SEQ ID NO: 5 or an intron fragment thereof, wherein nucleotide residues (each nucleotide is independently selected from A, T, G, and C) of about 1 to about 50 bp or about 10 to about 30 bp are added to 5'-end, 3'-end, or both ends of the intron or intron fragment.

IGKV (immunoglobulin kappa variable) intron refers to an intron region of a gene encoding a variable region of kappa light chain of an immunoglobulin. For example, the IGKV intron may be a human IGKV intron (e.g., an intron from position 269 to position 474 of Accession No. M27751.1 or X12688.1; 206 bp; SEQ ID NO: 6); an intron fragment comprising or consisting essentially of consecutive nucleotide residues of about 100 to about 206 bp, about 130 to about 206 bp, about 150 to about 206 bp, about 180 to about 206 bp, about 200 to about 206 bp, about 100 to about 205 bp, about 130 to about 205 bp, about 150 to about 205 bp, about 180 to about 205 bp, or about 200 to about 205 bp within SEQ ID NO: 6; an intron variant of the intron of SEQ ID NO: 6 or an intron fragment thereof, having a sequence identity of at least about 80%, at least about 85%, at least about 90%, at least about 95%, at least about 98%, or at least about 99%, with the sequence of the intron or intron fragment; or an intron variant of the intron of SEQ ID NO: 6 or an intron fragment thereof, wherein nucleotide residues (each nucleotide is independently selected from A, T, G, and C) of about 1 to about 50 bp or about 10 to about 30 bp are added to 5'-end, 3'-end, or both ends of the intron or intron fragment.

IGH (immunoglobulin heavy locus) intron refers to an intron region of a gene encoding a heavy chain of an immunoglobulin. The IGH intron may be obtained from any isotype of immunoglobulins, such as IgA, IgD, IgG, IgM, or IgE. For example, the IGH intron may be a human IGH intron (e.g., an intron from position 197 to position 278 of Accession No. M29811; 82 bp; SEQ ID NO: 7); an intron fragment comprising or consisting essentially of consecutive nucleotide residues of about 10 to about 82 bp, about 30 to about 82 bp, about 50 to about 82 bp about 10 to about 81 bp, about 30 to about 81 bp, or about 50 to about 81 bp, within SEQ ID NO: 7; an intron variant of the intron of SEQ ID NO: 7 or an intron fragment thereof, having a sequence identity of at least about 80%, at least about 85%, at least about 90%, at least about 95%, at least about 98%, or at least about 99%, with the sequence of the intron or intron fragment; or an intron variant of the intron of SEQ ID NO: 7 or an intron fragment thereof, wherein nucleotide residues (each nucleotide is independently selected from A, T, G, and C) of about 1 to about 50 bp or about 10 to about 30 bp are added to 5'-end, 3'-end, or both ends of the intron or intron fragment.

The chimeric intron may be an intron comprising or consisting essentially of the nucleotide sequence of SEQ ID NO: 8 (133 bp); an intron fragment comprising or consisting essentially of consecutive nucleotide residues of about 10 to about 133 bp, about 30 to about 133 bp, about 50 to about 133 bp, about 80 to about 133 bp, about 100 to about 133 bp, about 10 to about 132 bp, about 30 to about 132 bp, about 50 to about 132 bp, about 80 to about 132 bp, or about 100 to about 132 bp, within SEQ ID NO: 8; an intron variant of the intron of SEQ ID NO: 8 or an intron fragment thereof, having a sequence identity of at least about 80%, at least about 85%, at least about 90%, at least about 95%, at least about 98%, or at least about 99%, with the sequence of the intron or intron fragment; or an intron variant of the intron of SEQ ID NO: 8 or an intron fragment thereof, wherein nucleotide residues (each nucleotide is independently selected from A, T, G, and C) of about 1 to about 50 bp or about 10 to about 30 bp are added to 5'-end, 3'-end, or both ends of the intron or intron fragment.

In the fusion polynucleotide or fusion promoter, the intron may be linked to the 5'-end, 3'-end, or both ends (in case two or more introns, which is the same with or different from each other, are linked) of the murine CMV promoter. For example, the intron may be linked to 3'-end of the murine CMV promoter (i.e., the murine CMV promoter is located at 5'-terminal part and the intron is located at 3'-terminal part in the fusion protein). In the fusion polynucleotide or fusion promoter, the promoter and the intron may be linked to each other directly or via a proper linker. The linker may be any oligonucleotide, e.g., in length of about 2 to about 30 bp, about 2 to about 20 bp, or about 2 to about 10 bp, but not be limited thereto.

Another embodiment provides a method of preparing a fusion promoter, comprising linking an intron to the 5'-end or 3'-end (e.g., 3'-end) of a murine CMV promoter, or liking at least two introns, which are the same as or different from each other, to both ends of a murine CMV promoter. The fusion promoter may be capable of operating in an animal cell, for example, a mammalian cell. The details of the murine CMV promoter and intron are as described above.

The fusion polynucleotide or fusion promoter may function to effectively initiate transcription of a gene which is operatively linked thereto. The fusion polynucleotide or fusion promoter may be capable of effectively initiating transcription in any host cell, for example, a viral cell, a bacterial cell, or a eukaryotic cell, such as an insect cell, a plant cell, or an animal cell (e.g., a mammalian cell). For example, the fusion polynucleotide or fusion promoter may be capable of effectively initiating transcription in an animal cell, such as, a mammalian cell. The mammalian cell may be at least one selected from the group consisting of a mouse cell (e.g., COP, L, C127, Sp2/0, NS-0, NS-1, At20, NIH3T3, etc.), a rat cell (e.g., PC12, PC12h, GH3, MtT, etc.), a hamster cell (e.g., BHK, CHO, GS (glutamine synthetase) gene deficient CHO, DHFR (dihydrofolate reductase) gene deficient CHO, etc.), a monkey cell (e.g., COS1, COS3, COST, CV1, Vero, etc.), a human cell (e.g., Hela, HEK-293, PER C6 cell derived from retinal tissue, a cell derived from diploid fibroblast, myeloma cell, HepG2, etc.), hybridoma, and the like.

Another embodiment provides a recombinant vector comprising the fusion polynucleotide. The recombinant vector may be useful as an expression vector of a polypeptide of interest capable of highly expressing the fusion polynucleotide in a proper host cell, when a gene ("a gene of interest") encoding the polypeptide of interest is operatively linked to the fusion polynucleotide.

Another embodiment provides a recombinant vector comprising the fusion polynucleotide and a gene encoding a polypeptide of interest. In this case, the fusion polynucleotide may act as a promoter, and be operatively linked to the gene of interest. In one embodiment, the gene (polynucleotide) encoding the polypeptide of interest can be connected directly to an intron of the fusion polynucleotide/fusion promoter, or connected to a linker sequence that is connected to the intron, such that the intron is positioned between the gene encoding the polypeptide of interest and the CMV promoter or fragment thereof.

The term "vector" refers to a construct for expressing a target gene in a host cell. A vector may comprise elements necessary for expressing a gene of interest, such as a replication origin, a promoter, an operator, a terminator, and the like. In addition, a vector may further comprise at least one selected from the group consisting of an enzyme recognition site (e.g., a recognition (restriction) site of a restriction enzyme) for introducing a foreign gene into a genome of a host cell, a selection marker for confirming a successful introduction of the vector into a host cell, a ribosome binding site (RBS) for translation to a protein, an internal ribosome entry site (IRES), and the like. A vector may be genetically engineered so as to comprise the fusion polypeptide as a promoter. A vector may further comprise transcription control sequences (e.g., an enhancer) in addition to a promoter.

The vector may be exemplified by a plasmid vector, a cosmid vector, or a viral vector such as a bacteriophage vector, adenovirus vector, retrovirus vector, and an adeno-related virus vector. The recombinant vector may be constructed from, but not limited to, well-known plasmids (for example, pcDNA series (Invitrogen), pCI (Promega), Mammalian expression vector (Sigma), pCMV-Tag epitope taggging mammalian vector (Stratagene), pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc.), phages (for example, λgt4λB, λ-Charon, λAz1, M13, etc.), or viruses (for example, SV40, etc.), by manipulation.

In the recombinant vector, the gene of interest may be operatively linked to the fusion polynucleotide as a promoter. The term "operatively linked" is intended to pertain to a functional linkage between a nucleotide sequence (a gene) of interest and an expression regulatory element (for example, a promoter sequence) so that the expression of the nucleotide sequence of interest is controlled by the regulatory element. For instance, when the regulatory element such as a promoter is "operatively linked" to the nucleotide sequence (gene) of interest, it can control the transcription and/or translation of the nucleotide sequence (gene) of interest. In the recombinant vector, the fusion polynucleotide may be linked to 5'-end of a gene of interest, so that it can be operatively linked thereto.

The recombinant vector may be constructed by any method well-known in the art.

The recombinant vector may further comprise a transcription regulatory sequence in addition to a promoter. The transcription regulatory sequences may be at least one selected from the group consisting of a terminator, such as a polyadenylation sequence (pA); an origin of replication, such as an f1 origin of replication, an SV40 origin of replication, a pMB1 origin of replication, an adeno origin of replication, an AAV origin of replication, or a BBV origin of replication; and any combination thereof.

In addition, the recombinant vector may further comprise a selection marker. The selection marker may refer to a gene for confirming whether or not the recombinant vector is successfully introduced into a host cell or a stable recombinant cell comprising the recombinant vector is established. The selection marker may be a drug-resistant gene (e.g., an antibiotic-resistant gene), a metabolism-related gene, a gene amplifying gene, or any combination thereof. The selection marker may not affect the expression efficiency of the vector, and it can be any drug-resistant gene (e.g., an antibiotic-resistant gene) and/or a metabolism-related gene, which is generally used for a recombinant vector. For example, the selection marker may be at least one selected from the group consisting of an ampicilin-resistant gene, a tetracyclin-resistant gene, a kanamycin-resistant gene, a chloroamphenicol-resistant gene, a streptomycin-resistant gene, a neomycin-resistant gene, a blasticidin-resistant gene, a zeocin-resistant gene, a hygromycin-resistant gene, a puromycin-resistant gene, a thymidine kinase (TK) gene, a dihydrofolate reductase (DHFR) gene, a glutamine synthetase (GS) gene, and the like, but not be limited thereto.

An example of the recombinant vector is illustrated in FIG. 1.

Another embodiment provides a recombinant cell comprising the recombinant vector. The recombinant cell may refer to a cell transfected with the recombinant vector, i.e., a cell generated by introducing the recombinant vector into a host cell. The recombinant cell may further comprise a polynucleotide (a gene of interest) encoding a polypeptide of interest. In this case, a gene of interest may be introduced into the host cell together with the fusion polynucleotide (fusion promoter) (e.g., comprising a murine CMV promoter and an intron), through one recombinant vector (i.e., comprising the fusion promoter and a gene of interest) or two separate recombinant vectors (i.e., both comprising the fusion promoter and a gene of interest).

The host cell used in preparing the recombinant cell may be any animal cell (for example, any mammalian cell), wherein the fusion polynucleotide can act as a promoter (i.e., have a function to initiate transcription) and an expression of a gene of interest is allowed. For example, the host cell may be at least one mammalian cell selected from the group consisting of a mouse cell (e.g., COP, L, C127, Sp2/0, NS-0, NS-1, At20, NIH3T3, etc.), a rat cell (e.g., PC12, PC12h, GH3, MtT, etc.), a hamster cell (e.g., BHK, CHO, GS (glutamine synthetase) gene deficient CHO, DHFR (dihydrofolate reductase) gene deficient CHO, etc.), a monkey cell (e.g., COS1, COS3, COST, CV1, Vero, etc.), a human cell (e.g., Hela, HEK-293, PER C6 cell derived from retinal tissue, a cell derived from diploid fibroblast, myeloma cell, HepG2, etc.), and the like. The host cell may be isolated (separated) from a living body (i.e., not present in a living body).

Using a method well known in the art, the fusion polynucleotide or a recombinant vector carrying the fusion polynucleotide may be introduced (incorporated or transfected) into a host cell. For example, the transfection may be carried out through $CaCl_2$ or electroporation when the host cell is prokaryotic. For eukaryotic host cells, the genetic introduction may be performed using, but not limited to, microinjection, calcium phosphate precipitation, electroporation, liposome-mediated transfection, or particle bombardment.

To select a transfected host cell, advantage may be taken of the phenotype attributed to a selection marker according to a method known in the art. For example, when the selection marker is a gene resistant to a certain antibiotic as described above, the host cells may be grown in the presence of the antibiotic in a medium to select a transfected cell.

When the polypeptide of interest has an effect of preventing, treating, improving, and/or ameliorating a disease and/or a pathological condition, an embodiment provides a pharmaceutical composition comprising at least one selected from the group consisting of a recombinant vector comprising the fusion polynucleotide and a gene encoding the polypeptide of interest, a recombinant cell comprising the recombinant vector, and a culture (in a cell-containing or cell-free form) of the recombinant cell.

In another embodiment, provided is a use of the recombinant vector comprising the fusion polynucleotide and/or the recombinant cell comprising the recombinant vector, for increasing the production of a polypeptide of interest. In particular, provided is a composition for producing a polypeptide of interest, wherein the composition comprises a recombinant vector comprising the fusion polynucleotide and a gene encoding the polypeptide of interest which is operatively linked to the fusion polynucleotide, a recombinant cell comprising the recombinant vector, or a combination thereof.

Another embodiment provides a method of producing a polypeptide of interest using the recombinant vector and/or the recombinant cell.

For example, the method of producing a polypeptide of interest may comprise expressing a gene encoding a polypeptide of interest in the recombinant cell comprising the vector. The step of expressing a gene may be performed in vitro. The step of expressing a gene may comprise culturing the recombinant cell in a medium and under conditions allowing the expression of the gene in the cell, wherein the medium and conditions may be clear to the relevant art. In addition, the method may further comprise harvesting (obtaining or separating) the polypeptide of interest from the expressing or culturing product, after the step of expressing or culturing. The step of harvesting the polypeptide of interest may be performed by separating the polypeptide from the recombinant cell, a lysate thereof, and/or a culture media (in case the polypeptide is secreted to a medium). The method of producing may further comprise an additional step, such as a step of purification and/or modification, so that the harvested polypeptide can have a desired quality and/or purity.

As used herein, the term "polypeptide" refers to a molecule covering a polymer of amino acids which are linked to one another through peptide bond(s). The polypeptide may a polypeptide in any length; for example, the polypeptide may be a polypeptide comprising about 2 or more amino acids, such as a protein (e.g., comprising about 50 or more amino acids) or a peptide (e.g., comprising about 2 to about 49 amino acids).

The term "polypeptide of interest" may refer to a protein or a peptide having a desired activity (e.g., an activity of treating, preventing, and/or ameliorating a certain disease or symptom, and/or replacing a substance necessary in a living body) in a living body or a cell. For example, the polypeptide of interest may be at least one selected from the group consisting of proteins and peptides having an enzymatic activity (e.g., a protease, a kinase, a phosphatase, etc.), receptor proteins and peptides, transporter proteins and peptides, microbicidal and/or endotoxin-binding polypeptides, structural proteins and peptides, immunoglobulins, tissue plasminogen activators, toxins, antibiotics, hormones, growth factors, vaccines, and the like. The polypeptide of interest or the gene of interest may be intrinsic (i.e., originally present in a host cell) or extrinsic (i.e., introduced from out of a host cell), and in case the polypeptide or gene is extrinsic, it may be introduced from the same species or different species from the host cell.

In an embodiment, the polypeptide of interest may be at least one selected from the group consisting of a hormone, a cytokine, a tissue plasminogen activator, an immunoglobulin (e.g., an antibody or an antigen-binding fragment thereof or a variant thereof), and the like. The immunoglobulin (also refers to an antibody) may be any isotype (e.g., IgA, IgD, IgG, IgM or IgE), for example, IgG molecule (e.g., IgG1, IgG2, IgG3, or IgG4). The antigen-binding fragment refers to an antibody fragment possessing an antigen binding ability of the antibody, and may be comprise or consist essentially of at least about 20 amino acids, for example, at least about 100 amino acids. The antigen-binding fragment may be any fragment containing an antigen-binding region, and for example, it may be at least one selected from the group consisting of CDRs (complementarity determining regions), a Fab fragment, a Fab' fragment, a F(ab)2 fragment, a F(ab')2 fragment, a Fv fragment, a scFv fragment, a (scFv)2 fragment, a scFv-Fc fragment, a multibody containing various antigen-binding domains (e.g., a diabody, a triabody, a tetrabody, etc.), a single-domain antibody, an affibody, and the like. The variant of an antibody refers to a derivative of an antibody or an antibody fragment, which has an amino acid sequence modified from the amino acid sequence of an original antibody, with maintaining an antigen-binding ability of the original antibody. The antibody and/or antigen-binding fragment may be, but not limited to, animal antibodies (e.g., mouse-derived antibodies), chimeric antibodies (e.g., mouse-human chimeric antibodies), humanized antibodies, or human antibodies. The antibody or antigen-binding fragment may be isolated from a living body or non-naturally occurring (e.g., being synthetic or recombinant). The antibody may be monoclonal. When the polypeptide of interest is an antibody or antigen-binding fragment, the recombinant vector may comprise i) a gene encoding a heavy chain and/or a gene encoding a light chain, or gene encoding an antigen-binding fragment, and ii) a fusion promoter (fusion polynucleotide) which is operatively linked to the gene i). In this case, a gene encoding a heavy chain and a gene encoding a light chain may be carried together in one vector, or separately in different vectors. A recombinant vector containing both a gene encoding a heavy chain and a gene encoding a light chain, or at least two recombinant vectors, each of which contains each of a gene encoding a heavy chain and a gene encoding a light chain, can be introduced into a host cell. Alternatively, the polypeptide of interest may be at least one selected from the group consisting of insulin, human growth hormone (hGH), various growth factors, such as insulin-like growth factor, epidermal growth factor (EGF), vascular endothelial growth factor (VEGF), and the like, various receptors, tissue plasminogen activator (tPA), erythropoietin (EPO), cytokines (e.g., interleukin such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, and the like), interferon (IFN)-alpha, IFN-beta, IFN-gamma, IFN-omega or IFN-tau, tumor necrosis factors (TNF) such as TNF-alpha, TNF-beta or TNF-gamma, TRAIL, G-CSF, GM-CSF, M-CSF, MCP-1, and the like.

A gene encoding a polypeptide of interest (a gene of interest) may be intrinsic (i.e., originally present in a host cell) or extrinsic (i.e., introduced from out of a host cell), and in the case where the polypeptide or gene is extrinsic, it may be introduced from the same species as or a different species from the host cell. The details (e.g., a nucleotide sequence) of a gene of interest may be clearly defined by the described a polypeptide of interest.

In an embodiment, the polypeptide of interest may be an anti-c-Met antibody or an antigen-binding fragment thereof. For example, the anti-c-Met antibody may be the antibodies defined in Korean Patent Publication No. 2011-0047698, U.S. Pat. No. 8,563,696B2, which is the corresponding US patent thereof, and US Patent Publication No. 2013-0089542A1 (refer to Korean Patent Publication No. 2011-0047698, U.S. Pat. No. 8,563,696B2 and US Patent Publication No. 2013-0089542A1, the disclosures of which are incorporated in their entirety herein by reference), but not be limited thereto.

This disclosure may provide a recombinant vector for an animal cell (e.g., a mammalian cell) for high expression of a therapeutic protein or antibody, which can be useful in mass-production of various therapeutic proteins.

EXAMPLES

Hereafter, the present invention will be described in detail by examples.

The following examples are intended merely to illustrate the invention and are not construed to restrict the invention.

Example 1

Preparation of a Recombinant Vector

In this example, the expression of a protein of interest under regulation of a fusion promoter comprising a combination of a mouse CMV (mCMV) promoter and an intron was examined.

Figure 2:
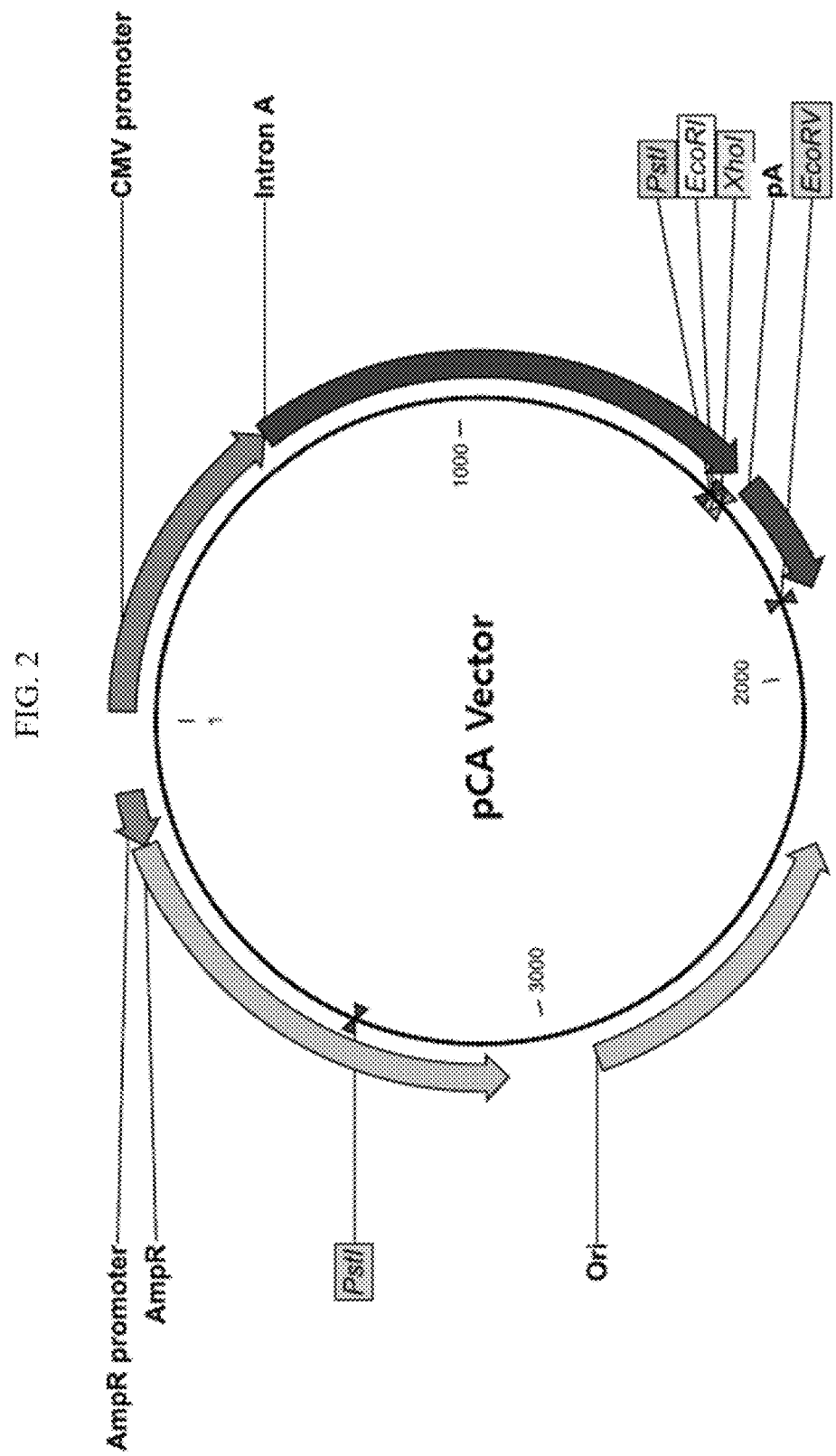
FIG. 2 is a cleavage map of pCA vector.
Figure 3:
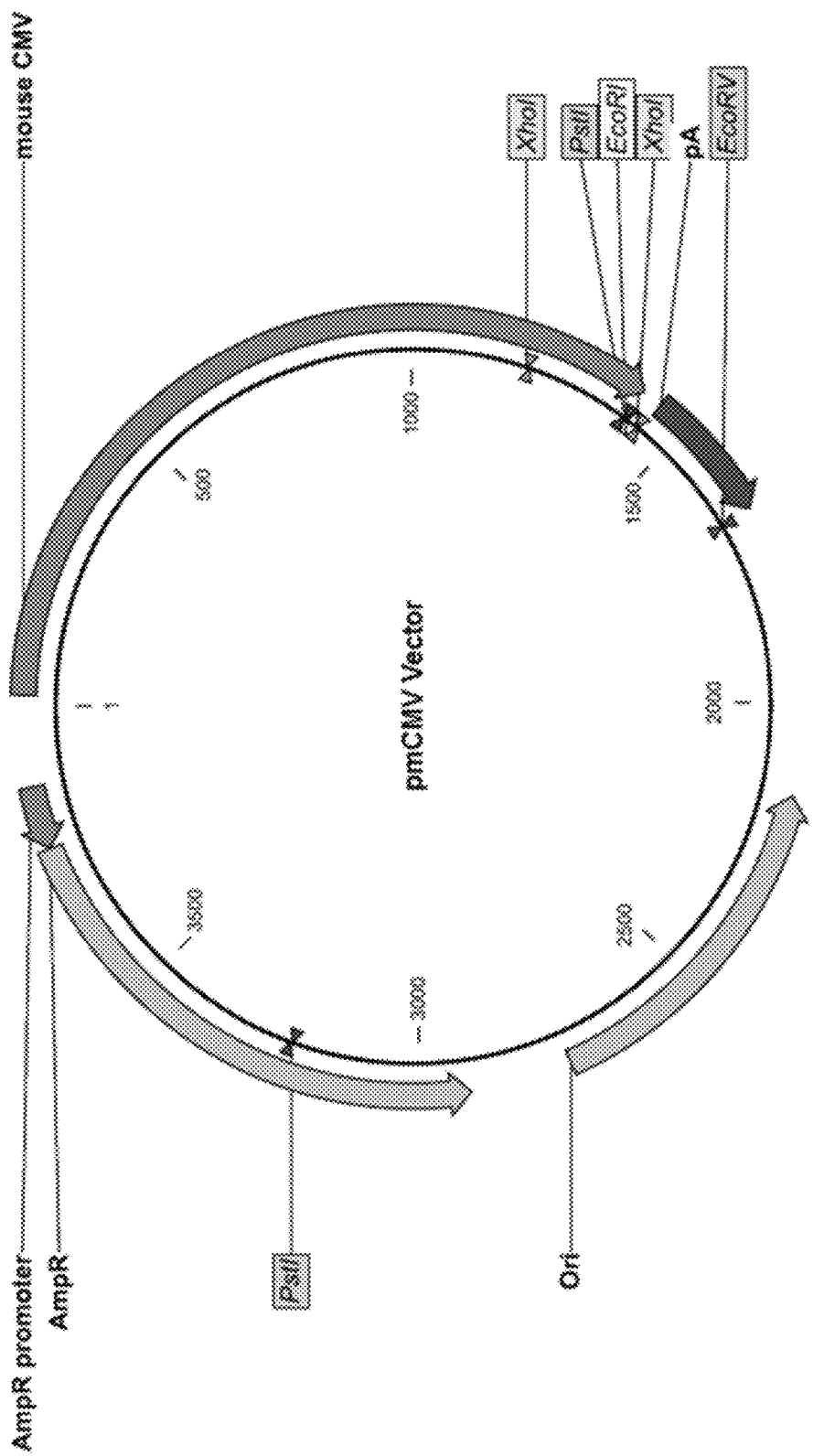
FIG. 3 is a cleavage map of pmCMV vector comprising a murine CMV promoter.

A mCMV promoter (SEQ ID NO: 9) was synthesized by gene synthesis. A pCA vector (FIG. 2) was provided, wherein a human CMV promoter and Intron A were removed using MluI/EcoRI, and the synthesized mCMV promoter was introduced into the MluI/EcoRI site, to construct a pmCMV vector (FIG. 3).

Figure 4:
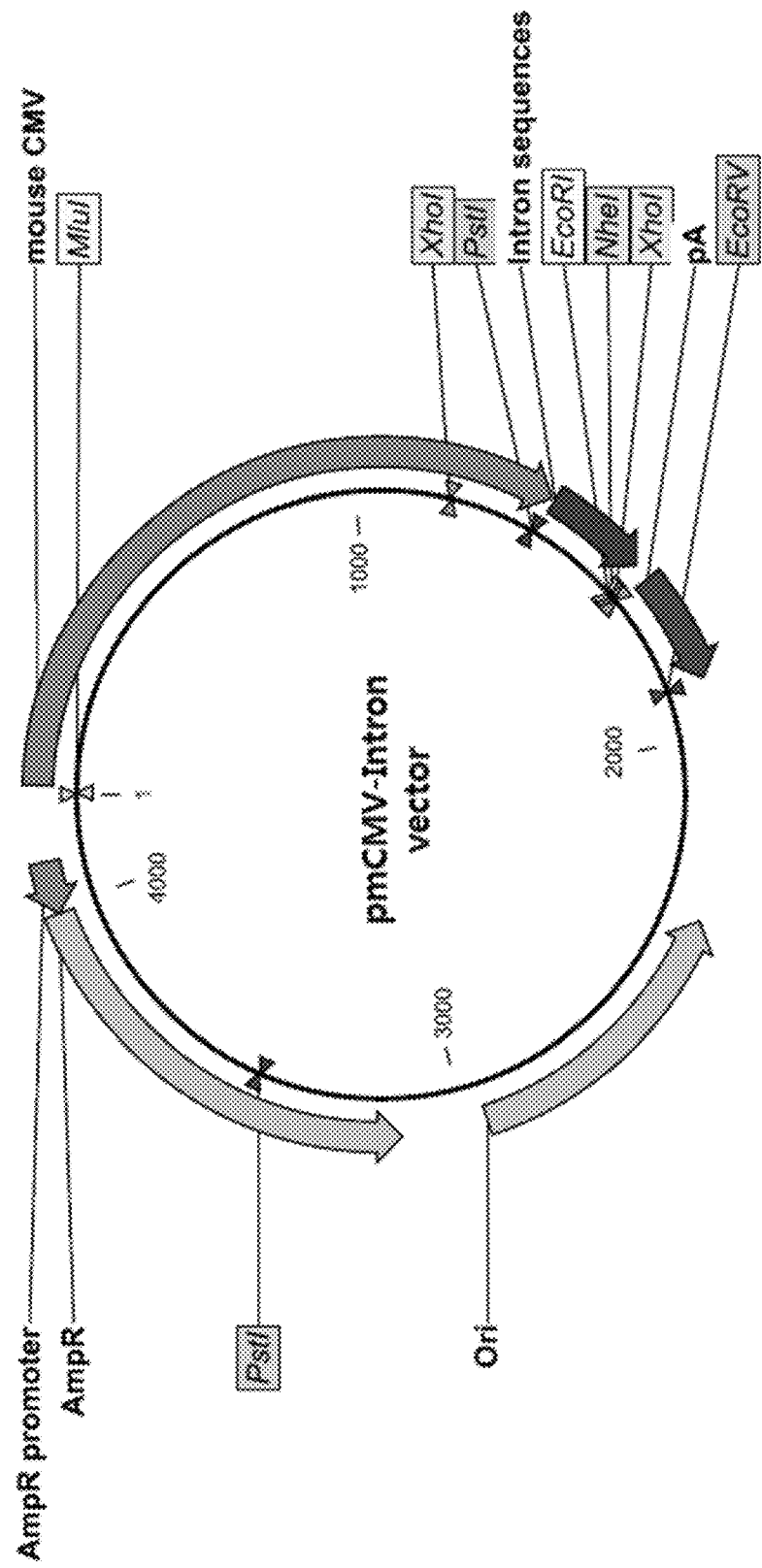
FIG. 4 is a cleavage map of pmCMV-Intron vector comprising a murine CMV promoter and intron.

Various introns were synthesized by gene synthesis (Table 1). A polymerase chain reaction (PCR) was performed using the synthesized intron as a template, and using forward primers (LInt-Fw, KInt-Fw, HInt-Fw, CInt-Fw: Table 2) containing a MfeI restriction site (5'-CAATTG-3') for amplifying 5' end region of an intron and a reverse primer (CA-Rv: Table 2) containing a XhoI restriction site (5'-CTCGAG-3') for amplifying 3' end region of an intron. The PCR was performed by 20 cycles under the conditions of 94° C. for 5 minutes, 94° C. for 30 seconds, 55° C. for 30 seconds, and 72° C. for 40 seconds, and then, elongation under the conditions of 72° C. for 5 minutes, to amplifying intron short fragments possessing a MfeI restriction site (5'-CAATTG-3') at 5' end and a XhoI restriction site (5'-CTCGAG-3') at 3' end. The obtained intron fragments were treated with MfeI and EcoRI restriction enzymes, and then, each was cloned into the obtained pmCMV vector at EcoRI site, to construct pmCMV-Intron vectors, each of which contains the fusion promoter of the mCMV promoter and each of the various introns (FIG. 4).

As a protein of interest, an anti-c-Met antibody was produced using the fusion promoter, to examine the efficiency thereof. The obtained pmCMV-Intron vectors containing the fusion promoter having various combination of the mCMV promoter and each of the various introns were treated with restriction enzymes EcoRI and XhoI, and then, cloned with a heavy chain coding polynucleotide (SEQ ID NO: 2) or a light chain coding polynucleotide (SEQ ID NO: 4) of an anti-c-Met antibody, to prepare a recombinant vector for expression of the heavy chain and a recombinant vector for expression of the light chain of the anti-c-Met antibody, respectively.

The introns used for the fusion promoter of mCMV promoter and intron are summarized in Table 1:

TABLE 1

| | | SEQ ID NO: |
|---|---|---|
| IGLV-1L1 Int (115 bP) | gtgacaggatggggaccaa gaaaggggccctgggaagc ccatggggccctgctttct cctatgtctccttttgtct cttgtcaatcaccatgtct gtgtctctctcacttccag | 5 |
| IGKV Int (206 bp) | gtgagaatatttagaaaaa gctaaaactaattctttga accattaattttcttaatt aggaacctggcaccatatg gaacttggcttgtttttaa atgtgatttttttttaagt aatgcgtattctttcatct tgtgctactagattagtgg tgatttcattaagcagatg cttatattgtgctaatgtt tgctgtatgttttcag | 6 |
| IGH Int (82 bp) | gtgagtgtctcagggatcc agacatgggggtatgggag gtgcctctgatcccagggc tcactgtgggtctctctgt tcacag | 7 |
| Chimeric Intron (133 bp) | gtaagtatcaaggttacaa gacaggtttaaggagacca atagaaactgggcttgtcg agacagagaagactcttgc gtttctgataggcacctat tggtcttactgacatccac tttgcctttctctccacag | 8 |

The primers used in the PCR were summarized in Table 2:

TABLE 2

Primers used in the PCR

| SEQ ID No. | Oligomer Name | Sequence |
|---|---|---|
| 10 | CA-Fw | 5'-taacagggtaatatag acgcgtgga-3' |
| 11 | LInt-Fw | 5'-agagctct caattg gtgacagga-3' |
| 12 | KInt-Fw | 5'-agagctct caattg gt gagaatat-3' |

TABLE 2-continued

Primers used in the PCR

| SEQ ID No. | Oligomer Name | Sequence |
|---|---|---|
| 13 | HInt-Fw | 5'-agagctct caattg gtga gtgtct-3' |
| 14 | CInt-Fw | 5'-agagctct caattg gtaagtatc-3' |
| 15 | CA-Rev | 5'-ttctcgagttctccgctagctcct-3' |

Example 2

Examination of the Expression of the Protein of Interest Using the Recombinant Vector The recombinant vectors (a recombinant vector for the heavy chain and a recombinant vector for the light chain of the anti-c-Met antibody) prepared in Example 1 were separated using Qiagen EndoFree Plasmid Mega kit (Cat no. 12381), and then introduced into a mammalian cell by transient transfection, and then, the amount of the protein (antibody) produced from the antibody-coding polynucleotides in the vectors was measured.

CHO-S cell line, which is a mutant generated from CHO-K1 cell line, was purchased from Invitrogen. CHO-S cells were grown in FreeStyle™ CHO expression medium supplemented with 8 mM Glutamine by suspension culture. The cells were seeded on a flask to the concentration of $2 \times 10^5$ cells/mL and segmented every 4 days. The flask was incubated at 36.5° C. under the conditions of 5% $CO_2$, 80% humidity, and 130 rpm. On one day before a transient gene expression, the cells were provided at the concentration of $5 \times 10^5$ cells/mL, and 24 hours after, when the concentration of the cells reached $1 \times 10^6$ cells/mL, a transfection was carried out.

90 mL of CHO-S cells were provided in 250 mL Erlenmeyer flask at the cell concentration of $1 \times 10^6$ cells/mL, and subjected to a transfection by liposomal reagent method using Freestyle™ MAX reagent (Invitrogen). Each of the recombinant vectors constructed in Example 1 were provided in a 15 ml tube so that the ratio of heavy chain DNA: light chain DNA reaches 1:1, and mixed with 2 ml of OptiPro™ SFM (Invitrogen) (tube A). A mixture of 100 μl of Freestyle™ MAX reagent and 2 ml OptiPro™ SFM was provided in another 15 ml tube (tube B). The tube A and tube B were mixed and incubated for 15 minutes, and the mixture solution was slowly dropped onto the provided cells to transfect the cells with the vectors. After completing the transfection, the transfected cells were incubated in an incubator under the conditions of 37° C., 80% humidity, 5% $CO_2$, and 130 rpm, for 5 days. Then, the supernatant was collected and the concentration of obtained anti-c-Met antibody therein was measured using a Protein A biosensor of Octet system (ForteBio). For comparison, the same experiment was performed using a vector with human CMV (hCMV; SEQ ID NO: 16; derived from pcDNA 3.3 TOPO vector (Invitrogen); a control) or mCMV only as a promoter.

Figure 5:
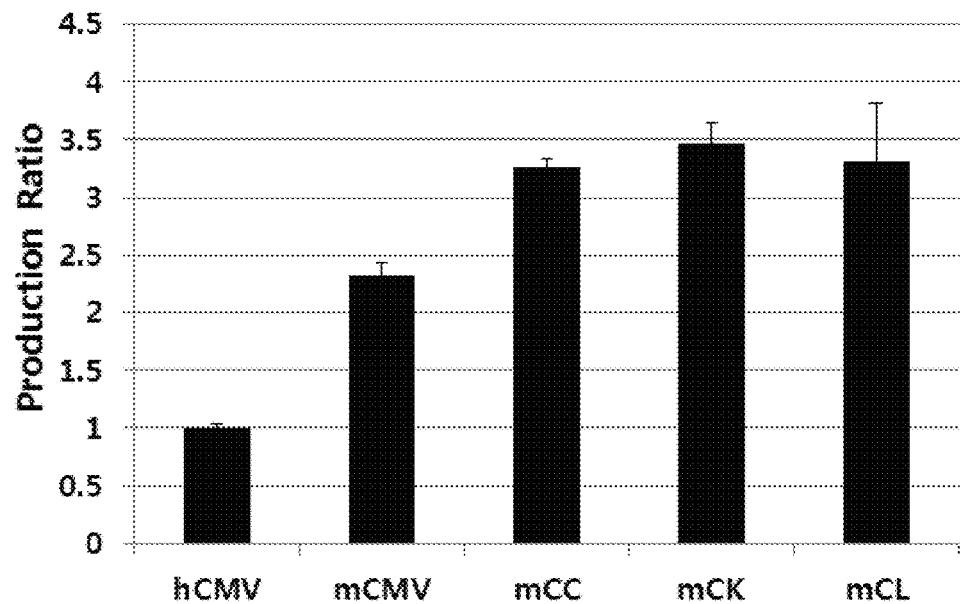
FIG. 5 is a graph showing an antibody production ratios when the antibody is expressed using a recombinant vector comprising a fusion polypeptide of a murine CMV promoter and intron in CHO cells (mCK: mouse CMV+IGK Intron; mCL: mouse CMV+IGLU intron) compared to that using a recombinant vector comprising a murine CMV promoter without an intron (hCMV: human CMV promoter, mCMV: mouse CMV promoter, mCC: mouse CMV+chimeric intron).

The measured antibody concentrations obtained using each fusion promoter are shown in FIG. 5, wherein the concentrations were indicated as a ratio to that of the control expression vector using hCMV promoter only (hCMV: human CMV promoter only, mCMV: mouse CMV promoter only, mCC: mouse CMV+chimeric intron, mCK: mouse CMV+IGK Intron, mCL: mouse CMV+IGLU intron). As shown in FIG. 5, compared to the control, antibody production level is considerably increased when the fusion promoter comprising the mCMV of SEQ ID NO: 9 and one of the various introns is used as a promoter.

What is claimed is:

1. A fusion polynucleotide comprising a murine CMV promoter and an intron, wherein the intron is linked to the 5'-end or 3'-end of the murine CMV promoter, wherein the murine CMV promoter consists of SEQ ID NO: 9, and wherein the intron is an immunoglobulin intron or a chimeric intron.

2. The fusion polynucleotide of claim 1, wherein the fusion polynucleotide comprises at least one of an IGLV intron, an IGKV intron, or an IGH intron.

3. The fusion polynucleotide of claim 1, wherein the intron comprises at least one of SEQ ID NOs: 5, 6, 7, or 8.

4. The fusion polynucleotide of claim 1, wherein the intron is linked to a 3'-end of the murine CMV promoter.

5. The fusion polynucleotide of claim 1, wherein the fusion polynucleotide comprises two introns, wherein one intron is linked to the 5'-end of the murine CMV promoter and one intron is linked to the 3'-end of the murine CMV promoter, and each intron is an immunoglobulin intron or a chimeric intron.

6. The fusion polynucleotide of claim 1, wherein the fusion polynucleotide comprises an IGLV intron or an IGKV intron.

7. The fusion polynucleotide of claim 6, wherein the fusion polynucleotide comprises SEQ ID NO: 5 or SEQ ID NO: 6.

8. A recombinant vector comprising the fusion polynucleotide of claim 1.

9. The recombinant vector of claim 8, further comprising a gene encoding a polypeptide of interest, wherein the gene encoding a polypeptide of interest and the fusion polynucleotide are operatively linked to each other.

10. The recombinant vector of claim 9, wherein the polypeptide of interest is an enzyme, a cell receptor polypeptide, a transporter polypeptide, a microbicidal or endotoxin-binding polypeptide, a structural polypeptide, an immunoglobulin, a tissue plasminogen activator, a toxin, an antibiotic, a hormone, a growth factor, a vaccine, or a combination thereof.

11. The recombinant vector of claim 10, wherein the polypeptide of interest is an antibody, wherein the fusion polynucleotide is operatively linked to at least one selected from the group consisting of a gene encoding a heavy chain of the antibody, a gene encoding a light chain of the antibody, and a gene encoding an antigen-binding fragment of the antibody.

12. The recombinant vector of claim 9, wherein the polypeptide of interest is an anti-C-Met antibody.

13. A recombinant cell comprising the recombinant vector of claim 8.

14. The recombinant cell of claim 13, wherein the recombinant vector further comprises a gene encoding a polypeptide of interest.

15. The recombinant cell of claim 13, wherein the host cell is a mammalian cell.

16. The recombinant cell of claim 14, wherein the polypeptide of interest is an enzyme, a cell receptor polypeptide, a transporter polypeptide, a microbicidal or endotoxin-binding polypeptide, a structural polypeptide, an immunoglobulin, a tissue plasminogen activator, a toxin, an antibiotic, a hormone, a growth factor, a vaccine, or a combination thereof.

17. The recombinant cell of claim 14, wherein the polypeptide of interest is an anti-C-Met antibody.

18. A method of producing a polypeptide of interest, comprising expressing the recombinant vector of claim 9 in a cell.

19. The method of claim 18, wherein the polypeptide of interest is anti-c-Met antibody.

20. The method of claim 18, wherein the polypeptide of interest is a an enzyme, a cell receptor polypeptide, a transporter polypeptide, a microbicidal or endotoxin-binding polypeptide, a structural polypeptide, an immunoglobulin, a tissue plasminogen activator, a toxin, an antibiotic, a hormone, a growth factor, a vaccine, or a combination thereof.

* * * * *

SEQUENCE LISTING

```
<160> NUMBER OF SEQ ID NOS: 16

<210> SEQ ID NO 1
<211> LENGTH: 460
<212> TYPE: PRT
<213> ORGANISM: Artificial Sequence
<220> FEATURE:
<223> OTHER INFORMATION: Synthetic (heavy chain of anti-c-Met antibody)

<400> SEQUENCE: 1

Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
```

115                 120                 125
Leu Val Thr Val Ser Ser Ala Ser Thr Lys Gly Pro Ser Val Phe Pro
            130                 135                 140
Leu Ala Pro Cys Ser Arg Ser Thr Ser Glu Ser Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
            180                 185                 190
Ser Ser Gly Leu Tyr Ser Leu Ser Ser Val Val Thr Val Pro Ser Ser
            195                 200                 205
Asn Phe Gly Thr Gln Thr Tyr Thr Cys Asn Val Asp His Lys Pro Ser
            210                 215                 220
Asn Thr Lys Val Asp Lys Thr Val Glu Arg Lys Cys Cys Val Glu Cys
225                 230                 235                 240
Pro Pro Cys Pro Ala Pro Pro Val Ala Gly Pro Ser Val Phe Leu Phe
                245                 250                 255
Pro Pro Lys Pro Lys Asp Thr Leu Met Ile Ser Arg Thr Pro Glu Val
                260                 265                 270
Thr Cys Val Val Val Asp Val Ser His Glu Asp Pro Glu Val Gln Phe
            275                 280                 285
Asn Trp Tyr Val Asp Gly Val Glu Val His Asn Ala Lys Thr Lys Pro
            290                 295                 300
Arg Glu Glu Gln Phe Asn Ser Thr Phe Arg Val Val Ser Val Leu Thr
305                 310                 315                 320
Val Val His Gln Asp Trp Leu Asn Gly Lys Glu Tyr Lys Cys Lys Val
                325                 330                 335
Ser Asn Lys Gly Leu Pro Ala Pro Ile Glu Lys Thr Ile Ser Lys Thr
            340                 345                 350
Lys Gly Gln Pro Arg Glu Pro Gln Val Tyr Thr Leu Pro Pro Ser Arg
            355                 360                 365
Glu Glu Met Thr Lys Asn Gln Val Ser Leu Thr Cys Leu Val Lys Gly
            370                 375                 380
Phe Tyr Pro Ser Asp Ile Ala Val Glu Trp Glu Ser Asn Gly Gln Pro
385                 390                 395                 400
Glu Asn Asn Tyr Lys Thr Thr Pro Pro Met Leu Asp Ser Asp Gly Ser
                405                 410                 415
Phe Phe Leu Tyr Ser Lys Leu Thr Val Asp Lys Ser Arg Trp Gln Gln
            420                 425                 430
Gly Asn Val Phe Ser Cys Ser Val Met His Glu Ala Leu His Asn His
            435                 440                 445
Tyr Thr Gln Lys Ser Leu Ser Leu Ser Pro Gly Lys
            450                 455                 460

<210> SEQ ID NO 2
<211> LENGTH: 1404
<212> TYPE: DNA
<213> ORGANISM: Artificial Sequence
<220> FEATURE:
<223> OTHER INFORMATION: Synthetic (polynucleotide encoding heavy chain
      of anti-c-Met antibody)

<400> SEQUENCE: 2
gaattcgccg ccaccatgga atggagctgg gttttcctcg taacactttt aaatggtatc        60
cagtgtgagg ttcagctggt ggagtctggc ggtggcctgg tgcagccagg gggctcactc       120

```
cgtttgtcct gtgcagcttc tggcttcacc ttcactgatt actacatgag ctgggtgcgt      180
caggccccgg gtaagggcct ggaatggttg ggttttatta gaaacaaagc taatggttac      240
acaacagagt acagtgcatc tgtgaagggt cgtttcacta agcagagata attccaaa       300 aacacactgt acctgcagat gaacagcctg cgtgctgagg acactgccgt ctattattgt      360
gctagagata actggtttgc ttactgggc caagggactc tggtcaccgt ctcctcggct       420
agcaccaagg gcccatcggt cttccccctg gcgccctgct ccaggagcac ctccgagagc      480
acagcggccc tgggctgcct ggtcaaggac tacttccccg aaccggtgac ggtgtcgtgg      540
aactcaggcg ctctgaccag cggcgtgcac accttcccag ctgtcctaca gtcctcagga      600
ctctactccc tcagcagcgt ggtgaccgtg ccctccagca acttcggcac ccagacctac      660
acctgcaacg tagatcacaa gcccagcaac accaaggtgg acaagacagt tgagcgcaaa      720
tgttgtgtcg agtgcccacc gtgcccagca ccacctgtgg caggaccgtc agtcttcctc      780
ttccccccaa aacccaagga caccctcatg atctcccgga cccctgaggt cacgtgcgtg      840
gtggtggacg tgagccacga agaccccgag gtccagttca actggtacgt ggacggcgtg      900
gaggtgcata atgccaagac aaagccacgg gaggagcagt tcaacagcac gttccgtgtg      960
gtcagcgtcc tcaccgttgt gcaccaggac tggctgaacg gcaaggagta caagtgcaag     1020
gtctccaaca aaggcctccc agcccccatc gagaaaacca tctccaaaac caaagggcag     1080
ccccgagaac cacaggtgta caccctgccc ccatcccggg aggagatgac caagaaccag     1140
gtcagcctga cctgcctggt caaaggcttc taccccagcg acatcgccgt ggagtgggag     1200
agcaatgggc agccggagaa caactacaag accacgcctc ccatgctgga ctccgacggc     1260
tccttcttcc tctacagcaa gctcaccgtg gacaagagca ggtggcagca ggggaacgtc     1320
ttctcatgct ccgtgatgca tgaggctctg cacaaccact acacgcagaa gagcctctcc     1380
ctgtctccgg gtaaatgact cgag                                            1404
```

<210> SEQ ID NO 3
<211> LENGTH: 240
<212> TYPE: PRT
<213> ORGANISM: Artificial Sequence
<220> FEATURE:
<223> OTHER INFORMATION: Synthetic (light chain of anti-c-Met antibody)

<400> SEQUENCE: 3

```
Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp Tyr Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125
```

```
Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 4
<211> LENGTH: 758
<212> TYPE: DNA
<213> ORGANISM: Artificial Sequence
<220> FEATURE:
<223> OTHER INFORMATION: Synthetic (polynucleotide encoding light chain
      of anti-c-Met antibody)

<400> SEQUENCE: 4
aattcactag tgattaattc gccgccacca tggattcaca ggcccaggtc tcatgttgc      60 tgctgctatc ggtatctggt acctgtggag atatccagat gacccagtcc ccgagctccc    120
tgtccgcctc tgtgggcgat agggtcacca tcacctgcaa gtccagtcag agtcttttag    180
ctagtggcaa ccaaaataac tacttggcct ggtaccaaca gaaaccagga aaagctccga    240
aaatgctgat tatttgggca tccactaggg tatctggagt cccttctcgc ttctctggat    300
ccgggtctgg gacggatttc actctgacca tcagcagtct gcagccggaa gacttcgcaa    360
cttattactg tcagcagtcc tacagccgcc cgtacacgtt cggacagggt accaaggtgg    420
agatcaaacg tacggtggct gcaccatctg tcttcatctt cccgccatct gatgagcagt    480
tgaaatctgg aactgcctct gttgtgtgcc tgctgaataa cttctatccc agagaggcca    540
aagtacagtg gaaggtggat aacgccctcc aatcgggtaa ctcccaggag agtgtcacag    600
agcaggacag caaggacagc acctacagcc tcagcagcac cctgacgctg agcaaagcag    660
actacgagaa acacaaagtc tacgcctgcg aagtcaccca tcagggcctg agctcgcccg    720
tcacaaagag cttcaacagg ggagagtgtt gactcgag                           758

<210> SEQ ID NO 5
<211> LENGTH: 115
<212> TYPE: DNA
<213> ORGANISM: Artificial Sequence
<220> FEATURE:
<223> OTHER INFORMATION: Synthetic IGLV-1L1 Intron

<400> SEQUENCE: 5
gtgacaggat ggggaccaag aaaggggccc tgggaagccc atggggccct gctttctcct      60
cttgtctcct tttgtctctt gtcaatcacc atgtctgtgt ctctctcact tccag          115

<210> SEQ ID NO 6
<211> LENGTH: 206
<212> TYPE: DNA
<213> ORGANISM: Artificial Sequence
<220> FEATURE:
<223> OTHER INFORMATION: Synthetic IGKV Intron
```

```
<400> SEQUENCE: 6
gtgagaatat ttagaaaaag ctaaaactaa ttctttgaac cattaatttt cttaattagg      60
aacctggcac catatggaac ttggcttgtt tttaaatgtg atttttttt aagtaatgcg      120 tattctttca tcttgtgcta ctagattagt ggtgatttca ttaagcagat gcttatattg    180
tgctaatgtt tgctgtatgt tttcag                                          206

<210> SEQ ID NO 7
<211> LENGTH: 82
<212> TYPE: DNA
<213> ORGANISM: Artificial Sequence
<220> FEATURE:
<223> OTHER INFORMATION: Synthetic IGH Intron

<400> SEQUENCE: 7
gtgagtgtct cagggatcca gacatggggg tatgggaggt gcctctgatc ccagggctca     60
ctgtgggtct ctctgttcac ag                                              82

<210> SEQ ID NO 8
<211> LENGTH: 133
<212> TYPE: DNA
<213> ORGANISM: Artificial Sequence
<220> FEATURE:
<223> OTHER INFORMATION: Synthetic Chimeric Intron

<400> SEQUENCE: 8
gtaagtatca aggttacaag acaggtttaa ggagaccaat agaaactggg cttgtcgaga     60
cagagaagac tcttgcgttt ctgataggca cctattggtc ttactgacat ccactttgcc    120
tttctctcca cag                                                        133

<210> SEQ ID NO 9
<211> LENGTH: 1391
<212> TYPE: DNA
<213> ORGANISM: Artificial Sequence
<220> FEATURE:
<223> OTHER INFORMATION: Synthetic mouse CMV promoter

<400> SEQUENCE: 9
aactccgccc gttttatgac tagaaccaat agttttaat gccaaatgca ctgaaatccc      60
ctaatttgca aagccaaacg cccccctatgt gagtaatacg gggactttttt acccaatttc  120 ccacgcggaa agcccctaa tacactcata tggcatatga atcagcacgg tcatgcactc     180
taatggcggc ccatagggac tttccacata ggggcgttc accatttccc agcatagggg    240
tggtgactca atggccttta cccaagtaca ttgggtcaat gggaggtaag ccaatgggtt   300
tttcccatta ctggcaagca cactgagtca aatgggactt ccactgggt tttgcccaag    360 tacattgggt caatgggagg tgagccaatg ggaaaaaccc attgctgcca agtacactga   420
ctcaataggg actttccaat gggttttcc attgttggca agcatataag gtcaatgtgg   480
gtgagtcaat agggactttc cattgtattc tgcccagtac ataaggtcaa taggggtga    540 atcaacagga aagtcccatt ggagccaagt acactgcgtc aatagggact ttccattggg   600
ttttgcccag tacataaggt caataggga tgagtcaatg gaaaaaccc attggagcca    660 agtacactga ctcaataggg actttccatt gggttttgcc cagtacataa ggtcaatagg   720
gggtgagtca acaggaaagt tccattggag ccaagtacat tgagtcaata gggactttcc   780
aatgggtttt gcccagtaca taaggtcaat ggaggtaag ccaatgggtt tttcccatta    840
```

-continued

| | |
|---|---|
| ctggcacgta tactgagtca ttagggactt tccaatgggt tttgcccagt acataaggtc | 900 |
| aatagggtg aatcaacagg aaagtcccat tggagccaag tacactgagt caatagggac | 960 |
| tttccattgg gttttgccca gtacaaaagg tcaataggg gtgagtcaat gggttttcc | 1020 |
| cattattggc acgtacataa ggtcaatagg ggtgagtcat tgggttttc cagccaattt | 1080 |
| aattaaaacg ccatgtactt tcccaccatt gacgtcaatg gctattgaa actaatgcaa | 1140 |
| cgtgacctttt aaacggtact ttcccatagc tgattaatgg gaaagtaccg ttctcgagcc | 1200 |
| aatacacgtc aatgggaagt gaaagggcag ccaaaacgta acaccgcccc ggttttcccc | 1260 |
| tggaaattcc atattggcac gcattctatt ggctgagctg cgttctacgt gggtataaga | 1320 |
| ggcgcgacca gcgtcggtac cgtcgcagtc ttcggtctga ccaccgtaga acgcagagct | 1380 |
| cctcgctgca g | 1391 |

<210> SEQ ID NO 10
<211> LENGTH: 25
<212> TYPE: DNA
<213> ORGANISM: Artificial Sequence
<220> FEATURE:
<223> OTHER INFORMATION: Synthetic CA-Fw primer

<400> SEQUENCE: 10
taacagggta atatagacgc gtgga                                  25

<210> SEQ ID NO 11
<211> LENGTH: 23
<212> TYPE: DNA
<213> ORGANISM: Artificial Sequence
<220> FEATURE:
<223> OTHER INFORMATION: Synthetic LInt-Fw primer

<400> SEQUENCE: 11
agagctctca attggtgaca gga                                    23

<210> SEQ ID NO 12
<211> LENGTH: 24
<212> TYPE: DNA
<213> ORGANISM: Artificial Sequence
<220> FEATURE:
<223> OTHER INFORMATION: Synthetic KInt-Fw primer

<400> SEQUENCE: 12
agagctctca attggtgaga atat                                   24

<210> SEQ ID NO 13
<211> LENGTH: 24
<212> TYPE: DNA
<213> ORGANISM: Artificial Sequence
<220> FEATURE:
<223> OTHER INFORMATION: Synthetic HInt-Fw primer

<400> SEQUENCE: 13
agagctctca attggtgagt gtct                                   24

<210> SEQ ID NO 14
<211> LENGTH: 23
<212> TYPE: DNA
<213> ORGANISM: Artificial Sequence
<220> FEATURE:
<223> OTHER INFORMATION: Synthetic CInt-Fw primer

<400> SEQUENCE: 14
agagctctca attggtaagt atc                                    23

<210> SEQ ID NO 15
<211> LENGTH: 24
<212> TYPE: DNA
<213> ORGANISM: Artificial Sequence
<220> FEATURE:
<223> OTHER INFORMATION: Synthetic CA-Rev primer

<400> SEQUENCE: 15
ttctcgagtt ctccgctagc tcct                                         24

<210> SEQ ID NO 16
<211> LENGTH: 680
<212> TYPE: DNA
<213> ORGANISM: Artificial Sequence
<220> FEATURE:
<223> OTHER INFORMATION: Synthetic hCMV promoter

<400> SEQUENCE: 16
gttgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggagt atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atggtgatgc ggttttggca gtacatcaat gggcgtggat     420
agcggtttga ctcacgggga tttccaagtc tccaccccat tgacgtcaat gggagtttgt     480
tttggcacca aaatcaacgg gactttccaa aatgtcgtaa caactccgcc ccattgacgc     540
aaatgggcgg taggcgtgta cggtgggagg tctatataag cagagctcgt ttagtgaacc     600
gtcagatcgc ctggagacgc catccacgct gttttgacct ccatagaaga caccgggacc     660
gatccagcct ccggactcta                                                680